Figure 1:
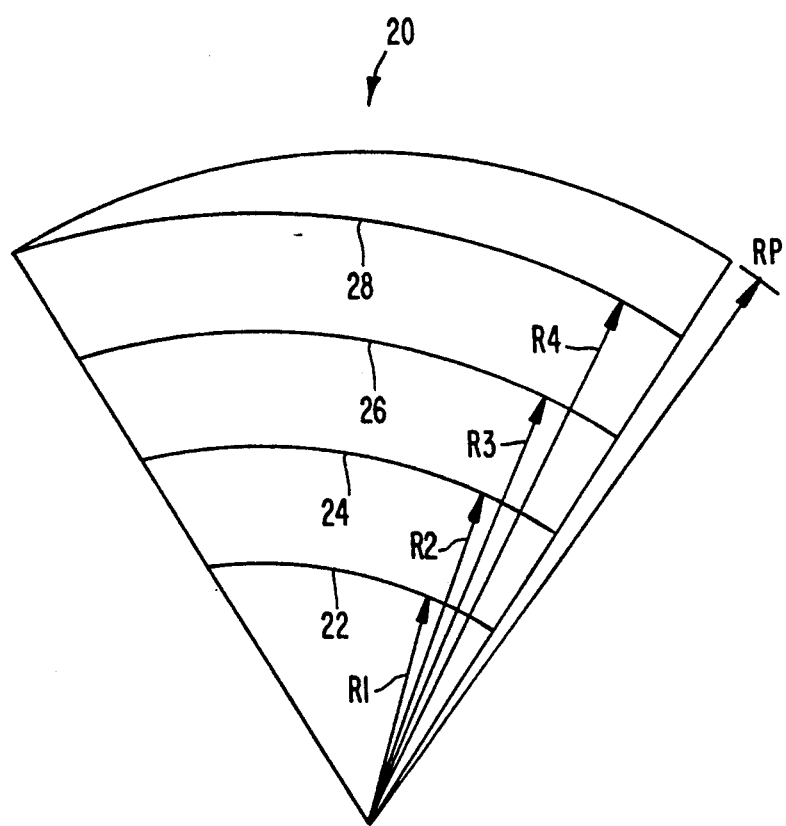

United States Patent [19]

Schalkowsky

[11] Patent Number: 5,246,837

[45] Date of Patent: Sep. 21, 1993

[54] PROCESSOR IMPLEMENTED METHOD FOR DETERMINING THE POTENCY OF A GROWTH AFFECTING SUBSTANCE INTERACTING WITH MICRO-ORGANISMS ON THE SURFACE OF MICROBIAL CULTURE MEDIA

[75] Inventor: Samuel Schalkowsky, Chevy Chase, Md.

[73] Assignee: Spiral System Instruments, Inc., Bethesda, Md.

[21] Appl. No.: 259,995

[22] Filed: Oct. 19, 1988

[51] Int. Cl.⁵ .......................... C12Q 1/18; C12Q 1/24
[52] U.S. Cl. ...................................... 435/29; 435/30; 435/32; 435/291; 435/809
[58] Field of Search ...................... 435/29, 30, 32, 291, 435/292, 293, 809

[56] References Cited

U.S. PATENT DOCUMENTS 4,514,495  4/1985  Schalkowsky et al. .............. 435/32
4,517,292  5/1985  Schalkowsky et al. .............. 435/32

OTHER PUBLICATIONS

Spiral System Instruments, Inc. of Bethesda, Md., Preliminary User Guide, titled "Determination of Antimicrobial Susceptibility by the Spiral Gradient Enpoint (SGE) Test", Jun. 1985.

Brochure for Spiral System Instruments, Inc. entitled "Reduce the Cost of Microbial Assays" (undated).

Primary Examiner—Karen M. Hastings
Attorney, Agent, or Firm—Antonelli, Terry, Stout & Kraus

[57] ABSTRACT

A method for determining an interacting culture medium concentration IAC of a growth-affecting substance in a volume of the culture medium related to growth of a microbial population deposited on a surface of the culture medium in accordance with the invention includes the steps of depositing the growth-affecting substance at a selected stock concentration SC in a programmed deposition on the surface of the culture medium such that the volume of the stock concentration at any deposited location on the surface of the culture medium is determinable; determining a transformation function TF which accounts for movement of the deposited growth-affecting substance through the culture medium; and calculating IAC as a function of SC and TF.

24 Claims, 5 Drawing Sheets

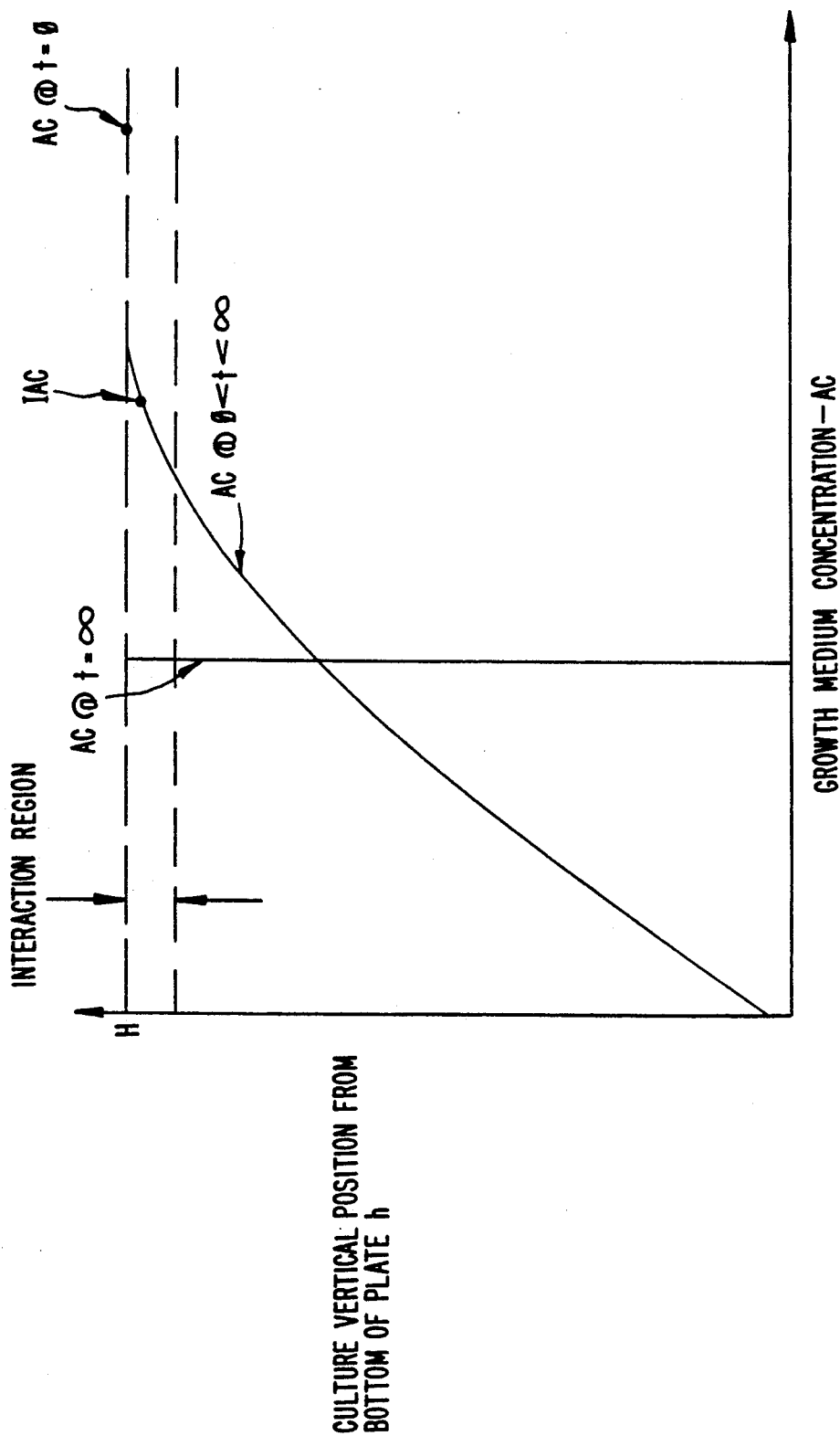

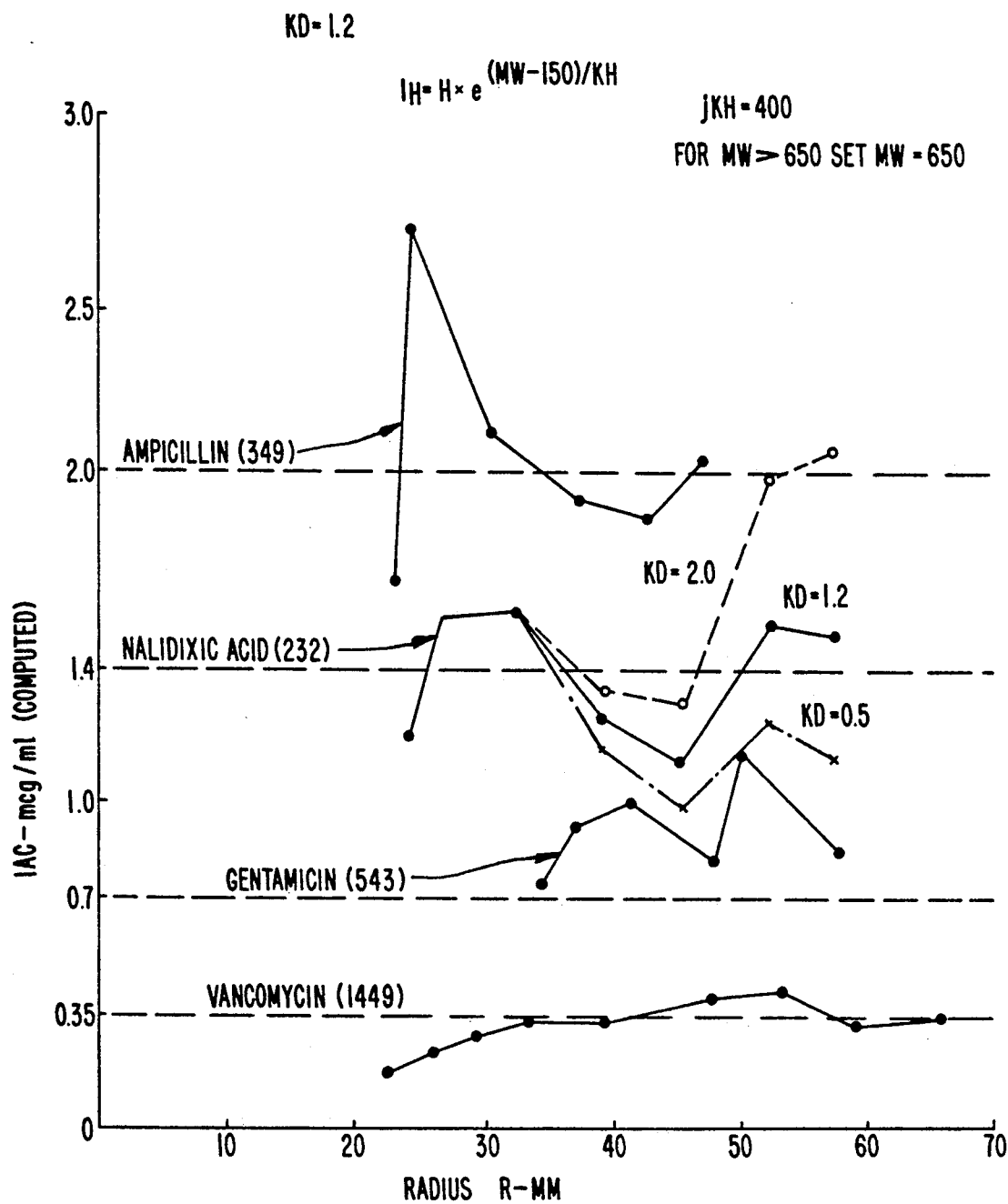

PROCESSOR IMPLEMENTED METHOD FOR DETERMINING THE POTENCY OF A GROWTH AFFECTING SUBSTANCE INTERACTING WITH MICRO-ORGANISMS ON THE SURFACE OF MICROBIAL CULTURE MEDIA

TECHNICAL FIELD

The present invention relates to methods for measuring the effect of growth-affecting substances on the properties of microbial populations and to the accurate quantitation of the relationship between the potency of the growth-affecting substance and changes in the population properties.

BACKGROUND ART

U.S. Pat. Nos. 4,514,495 and 4,517,292 disclose a method for depositing (1) a solution of a growth-affecting substance and (2) a microbe-containing solution, in a programmed manner onto the surface of a culture medium so as to allow for their interaction. In typical applications, the growth-affecting substance would be deposited to produce a gradient of potencies as a function of radial distance from the center while the microbe-containing solution would be deposited to provide the same concentration at all the selected locations on the culture plate. This permits the determination of the effect of different strengths (potencies) of the growth-affecting substance on the behavior of the microbial population. Measures of behavior could be the presence or absence of visible—or instrumentally detectable—colonies, or the number and/or size of such colonies.

A test in which an interaction property is the change from presence to absence of signs of growth on the culture medium is referred to as an endpoint test, where the "endpoint" is defined by the potency at which the transition from growth to no-growth occurs. Application of the procedures disclosed in the above-referenced patents to endpoint tests is described in the Spiral System Instruments, Inc. of Bethesda, Md. Preliminary User Guide, titled "Determination of Antimicrobial Susceptibility by the Spiral Gradient Endpoint (SGE) Test" and dated June, 1985. In this test the growth-affecting substance is an antimicrobial agent, i.e., a substance causing growth inhibition, deposited by means of the Spiral Plater TM, which is an instrument marketed by Spiral System Instruments, Inc. for depositing programmed gradients of solutions, to produce a radial gradient of potencies. The solution containing the test organism is deposited as a radial line on the surface by swabbing or by means of a mechanical inoculator. After incubation, there will be growth along the line of test sample deposited from the outside of the plate toward the center, stopping at the point along the line where the potency of the antimicrobial agent is sufficient to prevent visible growth. To quantify this effect it is necessary to determine the potency of the antimicrobial agent at the point of change from growth to no-growth.

A test in which the measure of the effect is the number of colonies developed as a function of the potency of the growth-affecting substance is the bacterial mutation assay, such as the popular Ames assay. In this test, the growth-affecting substance is the test compound, which is evaluated for its ability to produce mutations in selected bacterial strain(s). If a mutation occurs, then the cell will replicate and produce a colony (provided the compound is not toxic). The number of colonies is a measure of the degree of mutagenicity, which will vary with the potency of the compound to which the test strain is subjected.

The above-referenced patents are applied to bacterial mutagenicity testing by depositing a solution of the compound with the Spiral Plater TM to produce a radial gradient of potencies, and also depositing a solution containing the test strain with the Spiral Plater TM, but at a uniform concentration along the spiral deposition track. A count is made of the number of colonies developed in discrete segments of the spiral track, e.g., for each complete spiral. To obtain the desired dose-response information, it is also necessary to determine the average potency of the growth-affecting substance in each of the segments for which a colony count is made. See "Development and Validation of an Automated Approach to Bacterial Mutagenicity Testing," V. Houk, S. Schalkowsky & L. Clayton, poster paper presented at the annual meeting of Environmental Mutagen Society, Mar. 27–31, 1988 at Charleston, S.C.

There is a fundamental difference between the manner in which a growth-affecting substance and microbes combine with the culture medium after their deposition. Thus, while the microbes remain at or near the surface independent of elapsed time, the growth-affecting substance will diffuse radially as well as vertically downward after its deposition on the surface of the culture medium. The amount (weight) present at the surface as a function of elapsed time is a complex function of the physical properties of the substance, the potency gradient, properties of the culture medium into which diffusion takes place and environmental parameters, e.g., temperature. The method described in the above-referenced patents does not consider the above factors, and does not attempt to quantitate the potency at the surface where the interaction takes place. Instead it assumed that the surface potency can adequately be represented by a computation of the average weight of growth-affecting substance per unit volume of culture medium in the entire column of culture medium below the point of interaction on the plate, derived from the known volume of solution deposited by the Spiral Plater TM at any location along the track, the known weight of the growth-affecting substance per unit volume in this solution, and the height of culture medium in the plate.

The above average potency only approximates the actual surface potency and is useful in implementing the method of the above-referenced patents mostly because of the insensitivity of the test methods which are being replaced by it. Thus, standard endpoint tests as well as bacterial mutagenicity tests utilize a series of two-fold dilutions of the growth-affecting substance to test its effect on the same concentration of microbes. There is thus a 100% difference between the potencies of adjacent measurements and, when adding measurement uncertainties, a sensitivity of ±100% is usually associated with such tests. There is thus room within this range of variation of ±100% to accommodate some variation due to diffusion in the average potency value referred to in the above-referenced patents. The benefits of time and materials reductions, derivable from the methods disclosed in the above-referenced patents, are thus available. However, to also improve upon the accuracy and utility of test methods used to quantitatively assess the effect of microbial interactions with growth-affecting substances, it is necessary to know with accuracy the potency of the growth-affecting substance at specific locations on the surface of the culture medium. This requires the inclusion of diffusion effects in the determination of potency.

DISCLOSURE OF INVENTION

The present invention may be described in terms of the following relationship, with this relationship and other relationships defined below being programmed in a data processor in accordance with known programming techniques which are not part of the present invention:

$$IAC = SC \times TF \qquad (1)$$

IAC, the interacting culture medium concentration, is the quantity of interest which represents the weight of growth-affecting substance present per unit volume of culture medium at a selected location on the surface of the culture medium, to a depth needed to support the growth of the bacteria.

SC is the stock concentration of the growth-affecting substance, expressed as weight per unit volume of liquid, deposited in a programmed manner on the surface of the culture medium.

Figure 2:
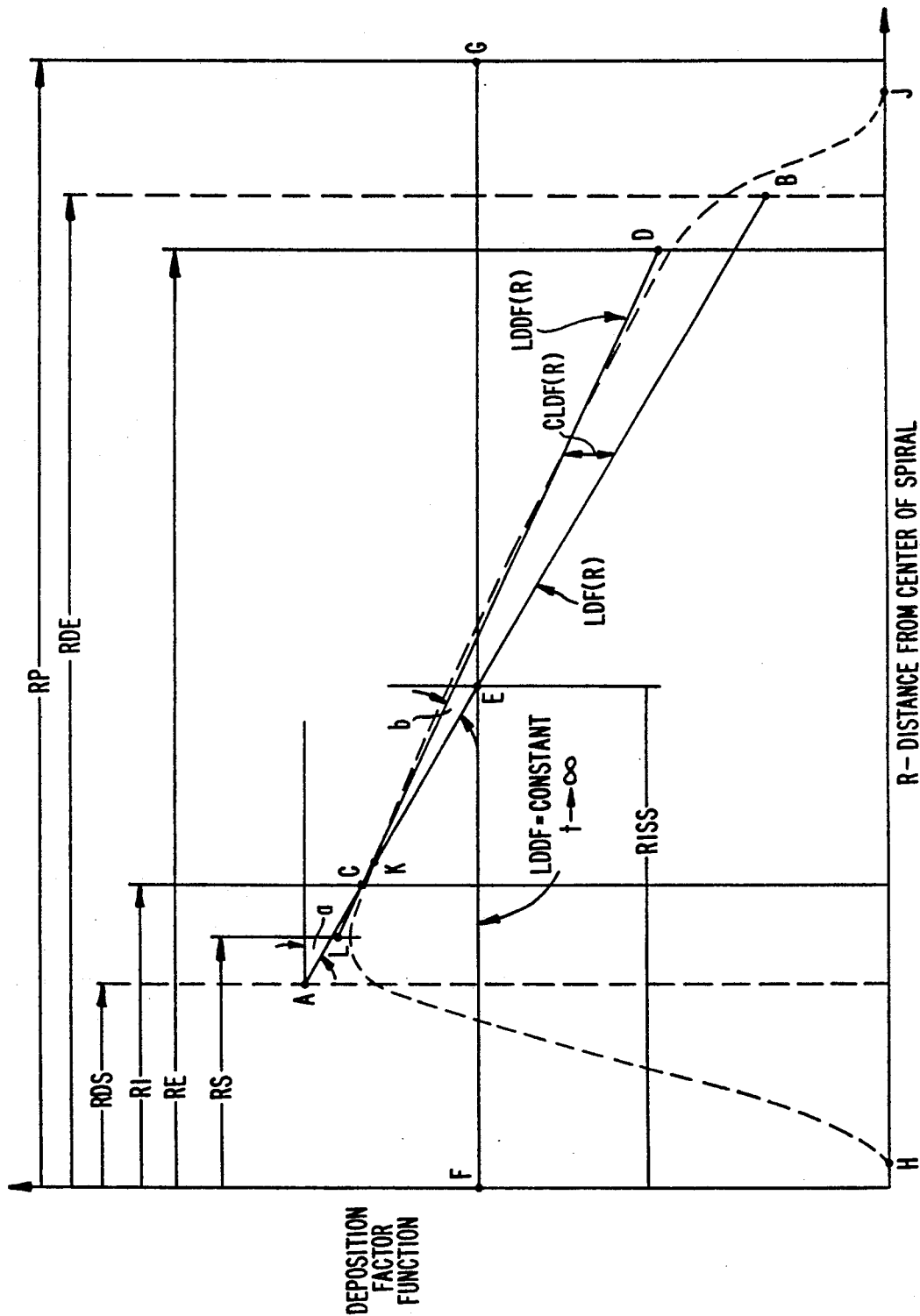

TF is the transformation function which, when multiplied by the known stock concentration, SC, provides the desired interaction culture medium concentration, IAC. The transformation function accounts for movement of the growth-affecting substance through the culture medium which is caused by effects such as but not limited to diffusion.

DF is the deposition factor which is defined as the volume of deposited stock solution, containing a known concentration (SC) of the growth-affecting substance, available per unit surface area of culture medium at the selected location on its surface. H denotes the height of the culture medium in the plate. In terms of these definitions, the transformation function in the above-referenced patents takes the form TF=DF/H. As such, it does not account for any changes in local potencies due to displacement of the growth-affecting substance with time.

This invention is based upon a different definition of TF by the inclusion of correction functions for the effect of diffusion. While a variety of such correction functions can be formulated to suit application requirements, the basic correction process can be defined as:

$$TF = \frac{DDF}{IH} \quad (2)$$

where DDF is a function of DF as well as of the molecular weight MW of the growth-affecting substance and parameter(s) whose value is to be determined from experimental data. Similarly, IH is a function of culture medium height, H, the molecular weight MW of the growth-affecting substance and experimentally determined parameters as described below.

Programmed deposition is an essential aspect of this invention as it provides a known functional relationship between the deposited volume of stock solution and location on the surface of the culture medium. The programmed deposition is implemented by known solution depositing apparatus such as the aforementioned Spiral Plater™ marketed by Spiral System Instruments, Inc. of Bethesda, Md., and described in the above-referenced patents. Since DF is programmed, and its rate of change with location therefore known, DF can be transformed to define a linear relationship with location on the surface of the culture medium. The linear DF function LDF serves as the reference function for obtaining DDF, the diffused concentration of growth-affecting substance on the surface of the culture medium as a function of location. First, a linear diffused deposition factor, LDDF, is obtained from the transformed LDF function. Inverting the linear transformation used to create the LDF function from the DF function yields the value of DDF from LDDF. Multiplying DDF by the known stock concentration of growth-affecting substance SC yields the diffused concentration of the substance at the selected location o the surface of the culture medium.

The interaction height, IH, is used to represent the effective depth of culture medium supporting the growth of the microorganisms as well as the effect of downward diffusion from the surface.

At time t=0, LDDF equals the transformed value of DF. After an infinitely long time, diffusion will cause LDDF to be the same everywhere in and on the culture medium. This steady-state value can be computed from the known total volume of deposited stock solution, the concentration of the growth-affecting substance in the stock solution and the volume of culture medium in the plate which contains the culture medium. For diffusion times greater than zero, of a magnitude determined by test conditions, the invention requires the formulation of an analytical relationship, with unknown parameters, to describe the manner in which LDDF relates to the transformed LDF value at the relevant locations on the culture medium. The above analytical relationship must include as one of its variables the molecular weight MW of the growth-affecting substance.

This invention further requires a corollary analytical relationship, with unknown parameters, to describe the manner in which the interaction height IH relates to the height of culture medium, H, and to the molecular weight MW of the growth-affecting substance.

The unknown parameters in the above two analytical relationships are found from (1) an independent determination of the interaction culture medium concentration, IAC, corresponding to the bacterial interaction property being measured and (2) repeat SGE (Spiral Gradient Endpoint) measurements of the same bacterial interaction property but at different stock concentrations SC of the growth-affecting substance. Since the interaction property being measured, e.g., growth endpoint, is the same in all the tests, changing the stock concentration SC has the effect of shifting the location of the measurement on the plate. Values of the unknown parameters are selected to yield the same interaction culture medium concentration IAC for all the different stock concentrations used. Stated differently, computed values of IAC will be the same regardless of the location on the plate where measurement is made with different values of stock concentration SC when the appropriate parameter values are used in the analytical formulations of DDF. Independent measurement of the "true" value of IAC permits determination of parameter values of the IH function so as to make the computed values of IAC equal the independently measured values.

A method for determining a concentration IAC in a volume of a culture medium of a growth-affecting substance affecting a growth of a microbial population deposited on a surface of the culture medium comprising the steps (1) depositing the growth-affecting substance at a selected stock concentration SC in a programmed deposition on the surface of the culture medium such that volume of the stock concentration at any deposited location on the surface of the culture medium is determinable; (2) determining a transformation function TF which accounts for movement of the deposited growth-affecting substance through the culture medium; and (3) calculating IAC as a function of SC and TF. Furthermore, preferably IAC=SC×TF. TF comprises a functional relationship of a plurality of quantities with one of the quantities being a function of the programmed deposition DF of the stock concentration. The quantity LDF is a linearization of the programmed deposition function DF. Further the invention includes determining a linearized diffused deposition function LDDF from the LDF to account for, at least in part, motion of the growth-affecting substance through the culture medium; and determining a diffused deposition function DDF from LDDF. DDF is a function of at least molecular weight MW of the growth-affecting substance. An angle (b) subtended by LDDF and LDF is a function of the molecular weight MW of the growth-affecting substance. Tangent (b)=kd/MW, wherein kd is a constant representing diffusion of the growth affecting substance in a particular set of physical and environmental factors. Another quantity is at least a function of the height of the culture medium. Further, the invention includes determining quantitative values of unknown parameters contained in TF. The determination of quantitative values of the unknown parameters is obtained from two sets of data with a first set of data being an independent determination of the IAC such that concentration of the growth-affecting substance for any data point is not affected by motion of the growth-affecting substance and a second set of data being obtained with the growth-affecting substance deposited in the programmed deposition with differing stock concentrations SC producing an identical IAC so as to alter the location of the interaction property on the surface of the culture medium. Values of some of the unknown parameters are selected such that the IAC for the second set of data have a low coefficient of variation. The values of some of the unknown parameters are selected such that the IACs of the second set of data for a particular growth affecting substance are approximately equal to the IAC of the first set. Preferably, the method of the present invention is implemented in a programmed data processor.

BRIEF DESCRIPTION OF DRAWINGS

FIG. 1 illustrates segments of spiral tracks of a growth-affecting substance as applied in a programmed manner to a culture medium;

FIG. 2 illustrates the relationship between deposition factor function of the growth-affecting substance and radial distance from the center of a plate on which the growth-affecting substance has been deposited in a manner such as illustrated in FIG. 1;

FIG. 3 illustrates the relationship of the culture medium height and the growth medium concentration AC;

FIG. 4 illustrates end points of visible microbial colonies which were cultured with growth-affecting substance of differing stock concentrations SC deposited on a culture medium with a spiral gradient of decreasing concentration with increasing radius;

FIG. 5 illustrates two successive cultures in which an independent verification of an IAC is made by using differing concentrations of a growth-affecting substance; and FIG. 6 illustrates the results of IAC versus radius obtained by experiments run in accordance with the invention.

BEST MODE FOR CARRYING OUT THE INVENTION

To facilitate description of the preferred embodiment, programmed deposition of the growth-affecting substance will be assumed to be in the form of a spiral pattern with decreasing rates of deposition from the center of a spiral located approximately at the center of a plate of culture medium outward toward the rim of the plate. It should be understood that preferably the computations described below in determining IAC are implemented in a programmed data processor in any suitable programming language. However, it should further be understood that the present invention is not limited to the implementation in a programmed data processor. FIG. 1 illustrates a chord of the surface of circular plate 20 on which tracks 22–28 of the growth-affecting substance have been deposited by a programmed deposition by an instrument such as the Spiral Plater™ marketed by Spiral System Instruments, Inc. as described in the above-referenced patents. The plate 20 is comprised of a culture medium such as agar which has been formed into a uniform thickness (not illustrated). Variation of the radius of deposition R results in the deposition tracks 22–28 respectively of radii R1–R4 which are part of a continuous spiral when the entire surface of the culture medium is viewed. The radius of the plate 20 is RP. When a specific formulation of the linearized deposition factor function, LDF, is required to facilitate definition of the method of the invention, it will be assumed that the rate of change of deposited volume as a function of radial distance from the center of the spiral is logarithmic. Neither of these assumptions is needed to define the invention, as other forms of programmed deposition are equally appropriate to its utilization. For example, a spirally deposited pattern can be used with the rate of change of deposited volume being directly proportional to the radial distance from the center of the spiral. Such a proportional LDF function is useful as a means of amplifying a portion of a logarithmic function.

FIG. 2 illustrates the relationship of the deposition factor function versus the radius of the spiral on which the growth-affecting substance has been deposited on the culture medium 20. In FIG. 2 RDS and RDE are, respectively, the initial and final deposition radii, i.e., the deposited stock is initially located only between points A and B of FIG. 1. The straight line between A and B is therefore the linearized deposition function LDF. The dotted line portions between points H and K and D and J illustrate the effect of movement of the growth affecting substance after deposition in a radial gradient.

For a logarithmic deposition rate, LDF would take the form:

$$LDF = LOG(D) = 1 \times S \times R \quad (3)$$

where I is the Y-axis intercept of the line AB and S is the slope; S=tan(a) wherein (a) is the angle subtended between the horizontal line segment emanating from point A and line AB.

The horizontal line FEG in FIG. 2 is the steady-state value of LDDF. Since the parameters I and S of the LDF function and the steady-state value of LDDF are known, the steady-state radius RISS associated with the intercept point E is readily computed.

The dashed curve HKJ in FIG. 2 illustrates the complex shape which the diffused deposition factor function can take on. Thus, the growth-affecting substance will diffuse from the high deposition region, near point A in FIG. 2, towards the center of the plate 20, where no stock was deposited, as well as toward the rim of the plate, because of the decreasing gradient of concentrations in the deposited region and initial absence of stock solution near the rim. The shape of this curve is a function not only of diffusion time, but also of the relevant physical parameters of the growth-affecting substance, such as molecular weight MW, and of the culture medium.

In the preferred embodiment of this invention, the diffused deposition factor function LDDF is defined as a linear function of distance, R, from the center of the spiral. Specifically, it is defined by the angle (b), which the LDDF line subtends above the LDF line, and its intercept C, with the LDF line. This linear LDDF function is restricted to a subregion of the initial deposition region, where it can be expected to reasonably approximate the more complex, actual shape of this function. The subregion extends from point L to point D, with associated starting and ending radii RS and RE, respectively.

The molecular weight MW of the growth-affecting substance is incorporated into the definitions of the angle b which the LDDF line makes with the LDF line:

$$\tan(b)=kd/MW \qquad (4)$$

kd represents the diffusion coefficient. Since the product of this coefficient and molecular weight is empirically known to be a constant, the value of kd can be expected to be constant for a given set of physical conditions acting on a particular growth-affecting substance.

As shown in FIG. 2, CLDF is the correction added to LDF to produce LDDF, i.e.

$$LEDDF=LDF+CLDF \qquad (5)$$

The solution for CLDF in terms of previously defined parameters is:

$$CLDF=\frac{R-RI}{\cos(a)\sin(a)\,[\sin(a)+\cos(a)\,MW/kd]} \qquad (6)$$

In the preferred embodiment of this invention, the intercept radius RI is set to a fixed value equal to or less than the steady-state value RISS. More complex formulations are readily defined, e.g., to make RI a function of molecular weight, but should not significantly enhance the accuracy of the method.

DDF is obtained from the known transformation of DF into LDF. For example, if LDF is as defined in equation (3), then DDF is the antilog of LDDF. From equations (3), (5) and (6), and neglecting sin(a) relative to the large MW/kd term, and neglecting sin(a)

$$LDDF=I-\tan(a)\times R+\frac{R-RISS}{\cos(a)\sin(a)\cos(a)\,MW/kd} \qquad (7)$$

Inverting the linear transformation used to create the LDF function from the DF function will then yield the value of DDF from LDDF.

The interaction height function IH is obtained by curve fitting to the experimental data in terms of a parameter kh, the culture medium height H and the molecular weight of the growth-affecting substance.

Given the stock concentration SC, which is available from the programmed deposition of the growth-affecting substance, DDF which has been determined from the LDDF, and IH, the IAC is solved for by use of equations (1) and (2) above.

FIG. 3 illustrates the variation of the concentration of the growth-affecting substance AC with location in the culture medium h- as measured from the bottom of the plate 20- for a selected position on the surface of the plate. H is the total depth of culture medium, i.e. it is the thickness of culture medium. In FIG. 3, H represents the selected position on the surface. The dashed horizontal lines at and just below h=H show the interaction region of interest, i.e. the depth of culture medium in which the growth-affecting substance has its principal effect on the deposited microbial population. IAC represents the concentration of the growth-affecting substance in the interaction region. A time t=0, there has not as yet been any displacement of the growth-affecting substance; it is therefore concentrated at the surface location only, as illustrated in FIG. 3 by AC@t=0. In the steady-state, when an infinite time has elapsed, the growth-affecting substance is uniformly distributed throughout the culture medium, as illustrated by the vertical line in FIG. 3 for AC@t=∞. At any interim time interval, the growth-affecting substance will have different concentrations at different vertical locations from the bottom of the plate. This is illustrated in FIG. 3 by the curve identified as AC@0<t<∞. The variation concentration with vertical position thus changes from a surface concentration at time zero, to variable concentrations as a function of vertical position for times greater than zero, progressing toward the constant concentration with vertical position (as well as radial location) in the steady-state. IAC, the quantity of interest, is the average concentration of the growth-affecting substance over the interaction time in the interaction region. The quantity IH serves to incorporate the variations illustrated in FIG. 3 into the computation of IAC.

The principal parameters to be determined experimentally are thus kd and kh; in addition, RS and RE are selected as the upper and lower bounds of R for which the principal parameter values remain valid.

Experimental evaluation of the principal parameters for a particular diffusion time interval (determined by the test procedure under evaluation) involves a range of growth-affecting substances—represented by their molecular weights. The same parameter values apply to test procedures involving a comparable length of time for the relevant interaction process. For example, the same set of parameter values would be used in antimicrobial susceptibility tests of a variety of bacterial isolates, but all having comparable division times and therefore also similar incubation periods. The same parameter set could thus be used for testing aerobic bacteria requiring overnight incubation, but a different set may be desirable for anaerobes which are incubated for 2 or more days. Similarly, parameter values appropriate to the relatively short mutation interval in a bacterial mutagenicity test may not be appropriate to the measurement of toxicity effects in such a test, which may involve longer interaction times; experimental determinations would therefore have to be based on different interaction measures and could result in different sets of parameter values.

Figure 4:
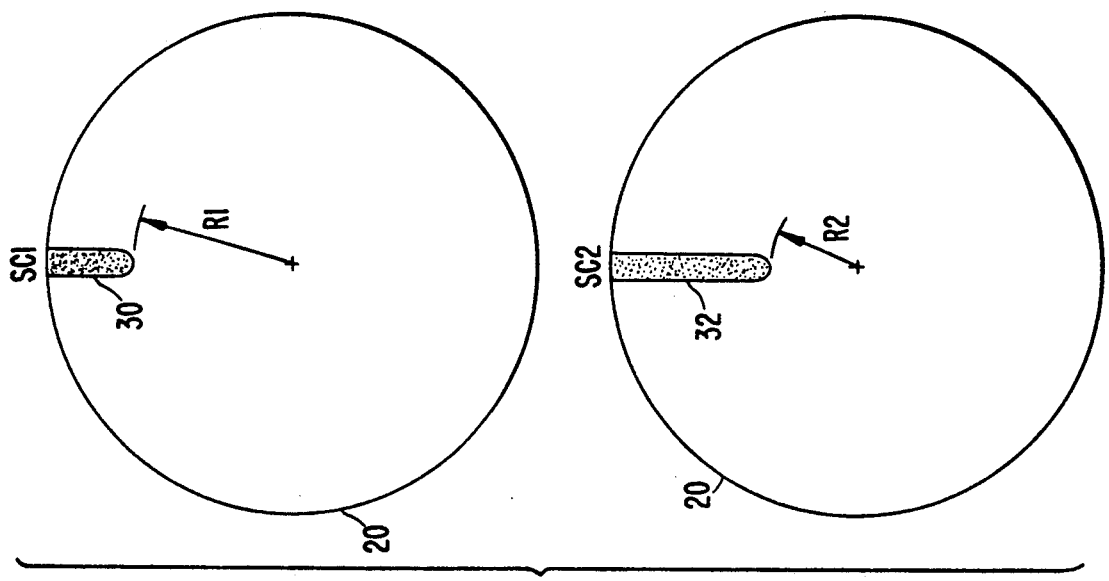

Determination of parameter values from experimental data consists of computed IAC values for the various stock concentrations SC used in obtaining the data, based upon selected values of kd and assuming, initially, that IH=H. FIG. 4 illustrates the endpoints where visible microbial colonies 30 and 32 stop on plate 20 which were prepared with differing stock concentrations SC with the growth affecting substance being applied in a spiral gradient with decreasing concentration as the deposition radius increases. The value of kd is changed until the computed IAC's for each molecular weight are all approximately equal to each other. A functional relationship is then constructed on the basis of the data, in terms of H, molecular weight and a correction parameter kh, so as to make the computed IAC's for each molecular weight approximately equal to its independently determined culture medium concentration. The desired parameter values will thus be obtained when the computed IAC's for the various stock concentration measurements are the same, i.e., they are independent of location on the plate, and are also equal to the value obtained under conditions which do not involve diffusion of the growth-affecting substance. The boundaries RS and RE are determined from observation of the range of R for which the coefficient of variation of the computed IAC's is acceptably small.

EXAMPLE

The following illustration of the preferred embodiment of the invention relates to the testing of the susceptibility of aerobic bacteria to antimicrobial agents. Such tests are conducted with standardized inoculum size, type of culture medium used and related incubation and handling procedures. In this example, the SGE test referred to above would be used to determine the IAC at the point of transition from growth to no-growth.

It is to be noted that the interaction property to be determined independently for this example is a growth endpoint. This differs from the standard minimum inhibitory concentration (MIC) test which seeks the first concentration, in a series of increasing two-fold concentrations of the growth-affecting substance, to show no-growth. In the latter case, the interaction property to be determined independently would be the no-growth MIC endpoint.

The antimicrobial agents, their molecular weights and the strains of bacteria used are summarized below:

| Drug | Mol. Weight | Test Strain |
|---|---|---|
| Nalidixic Acid | 232 | E. coli ATCC 25922 |
| Ampicillin | 349 | E. coli ATCC 25922 |
| Gentamicin | 543 | P. aeruginosa ATCC 27853 |
| Vancomycin | 1449 | S. aureus ATCC 29213 |

Spiral plating of the drugs was done with a logarithmic variation of deposited volume versus radius with a Spiral Plater ™ referenced above. Using logarithms to the base 2, expressing the radius R in mm and the deposition factor DF in microliters/square mm, the linearized deposition factor function was $$LDF\ LOG2(DF) = -1.835 - 0.191 \times R \tag{8}$$

which derives from the known deposition factor function $$DF = 2^{-1.835 - 0.191 \times R} \tag{9}$$

Since deposition was started at a radius of 13 mm and ended at a radius of 64 mm, RDS=13 and RDE=64.

The total volume of stock concentration SC deposited by the Spiral Plater ™ was 52.5 microliters and the inside diameter of the plate was 136 mm. The steady-state deposition factor was computed as 52.5 divided by a total agar area of 14,527 square mm, which equals 0.0036 microliters/square mm. From equation (9), the corresponding steady-state intercept radius is RISS=33.1 mm.

The slope of DF, as shown in equation (8), is 0.191. This corresponds to an angle a=10.8 degrees. Setting RI=RISS and neglecting small terms, LDDF becomes (see equation 7):

$$LDDF = -1.835 - 0.191 \times R + \frac{R - 33.1}{.184 \times MW/kd} \tag{10}$$

Since logarithms to the base 2 were used in defining LDF, DDF can be written as:

$$DDF = DF \times 2^{5.44 \times [R - 33.1] \times [kd/MW]} \tag{11}$$

Figure 5:
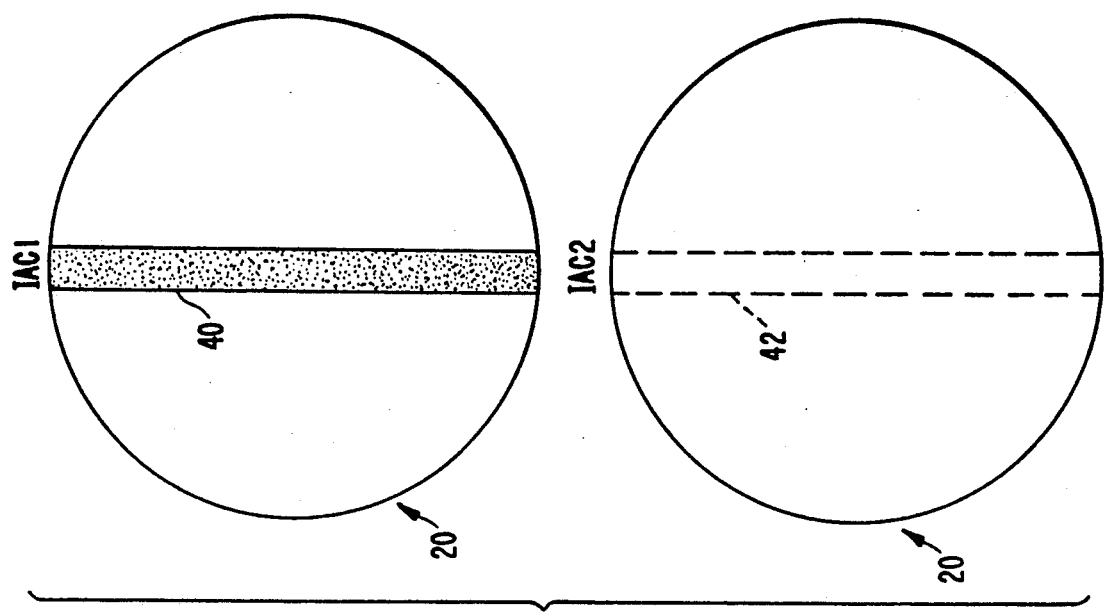

The independent determination of growth endpoint agar concentrations consisted of incorporating fixed amounts of each antibiotic in a series of 10 plates in increments of about 20%, covering the range where the "true" IAC was expected to fall. This process is illustrated in FIG. 5 with IAC 1 being the last in a series of increasing concentrations in which microbial growth 40 was not inhibited and IAC 2 being the first in this series of concentrations in which microbial growth was inhibited with the area 42 being an area which was inoculated with microbes which did not display visible growth. The endpoint value thus obtained will be referred to as the TIAC, to differentiate it from the CIAC—the computed IAC, which are based on the observed endpoint location on SGE plates and the selected parameter values for kd and kh.

SGE plates were prepared for each antibiotic with about ten different stock concentration values, to produce endpoint readings over a wide range of locations on the plate. (The number of actual endpoint readings obtained from such a series was limited by the solubility of the antibiotic, which in some instances precluded obtaining readings in the outer region of the plate. In other instances, readings near the center of the plate were not available because of the choice of the lowest stock concentration values.)

FIG. 6 illustrates the results of the parameter determination procedure. Referring to FIG. 6, the dashed horizontal lines represent the TIAC values for the antibiotic whose name is written above it (numbers in parentheses are the associated molecular weights). The four solid-line curves represent the CIAC values computed from DDF/IH, using the selected kd value, and the fitted functional relationship for IH and its associated kh value. As shown in FIG. 6, these curves display the desired behavior in that (1) the CIAC's are generally close to their TIAC's and (2) the CIAC values are largely independent of radial position on the plate.

The above results were obtained in two discrete steps. First IH was set to be equal to H only, which is the thickness of the culture medium on the plate, i.e., CIAC was computed from DDF/H. This permitted the selection of kd by observing whether the CIAC's computed in this matter were largely independent of position R, without regard to the differences between CIAC and TIAC. This is most conveniently done by plotting the CIAC values versus R. As illustrated in FIG. 6 for nalidixic acid, the choice of kd=1.2 gave the desired pattern, while kd=0.5 and kd=2.0 produced, respectively, decreasing and increasing CIAC's with R.

Setting IH=H also provided a base of data for developing the IH function and for selecting its kh value. Specifically, by plotting the means for the CIAC/TIAC ratios over all values of R for each of the four antibiotics, it was found that a suitable form for IH is:

$$IH = H \times e^{[MW-150]/kh} \quad (12)$$

with kh=400 and provided that MW is set to 650 if MW>650. These choices are reflected in the final results shown in FIG. 2.

The following table provides a quantitative representation of the graphical results shown in FIG. 6.

| | MEAN CIAC/TIAC | CIAC COEFF. OF VARIATION |
|---|---|---|
| Nalidixic Acid (232) | 0.99 | 14.0% |
| Ampicillin (349) | 1.03 | 18.0% |
| Gentamicin (543) | 1.21 | 26.1% |
| Vancomycin (1449) | 0.86 | 21.5% |

A ratio of 1.0 is obtained when the computed IAC values are equal to the "true" IAC's; independence from radial position on the plate is reflected in low coefficients of variation.

Based upon the final results shown in FIG. 6, the region from RS=20 to RE=64 was judged suitable for the utilization of the diffusion correction equations and associated parameter values.

While the invention has been disclosed in terms of its preferred embodiment, it should be understood that numerous modifications may be made without departing from the spirit and scope of the invention as defined in the appended claims. It is intended that all such modifications fall within the scope of the appended claims.

I claim:

1. A method implemented by a programmed data processor for determining a concentration IAC in a volume of a culture medium of a growth-affecting substance affecting a growth of a microbial population deposited on a surface of the culture medium comprising the steps:

depositing the growth-affecting substance at a selected stock concentration SC in a programmed deposition on the surface of the culture medium such that volume of the stock concentration at any deposited location on the surface of the culture medium is determinable;

determining a transformation function TF which accounts for movement of the deposited growth-affecting substance through the culture medium; and calculating IAC at a point of interaction on the culture medium of an interaction of the growth-affecting substance and the microbial population with IAC being a weight per unit volume of the growth-affecting substance at the point of interaction on the culture medium wherein IAC=SC×TF.

2. A method in accordance with claim 1 wherein:

TF comprises a functional relationship of a plurality of quantities with one of the quantities being a function of the programmed deposition DF of the stock concentration.

3. A method in accordance with claim 2 wherein:

the one quantity LDF is a linearization of the programmed deposition function DF.

4. A method in accordance with claim 3 further comprising:

determining a linearized diffused deposition function LDDF from the LDF to account for motion of the growth-affecting substance through the culture medium; and determining a diffused deposition function DDF from LDDF.

5. A method in accordance with claim 4 wherein:

DDF is a function of at least molecular weight MW of the growth-affecting substance.

6. A method in accordance w with claim 5 wherein:

an angle (b) subtended by LDDF and LDF is a function of the molecular weight MW of the growth-affecting substance.

7. A method in accordance with claim 6 wherein:

$$\tan(b) = \frac{kd}{MW}$$

wherein kd is a constant representing diffusion of the growth-affecting substance in a particular set of physical and environmental factors.

8. A method in accordance with claim 5 wherein:

another quantity is at least a function of the height of the culture medium.

9. A method in accordance with claim 1 further comprising:

determining quantitative values of unknown parameters contained in TF.

10. A method in accordance with claim 9 wherein the determination of quantitative values of the unknown parameters is obtained from two sets of data with a first set of data being an independent determination of IAC such that concentration of the growth-affecting substance for any data point is not affected by motion of the growth-affecting substance and a second set of data being obtained with the growth-affecting substance deposited in the programmed deposition with differing stock concentrations SC producing an identical IAC so as to alter a location of the point of interaction on the surface of the culture medium.

11. A method in accordance with claim 10 wherein:

the values of some of the unknown parameters are selected such that IAC for the second set of data have a coefficient of variation.

12. A method in accordance with claim 11 wherein:

the value of some of the unknown parameters are selected such that IAC of the second set of data are approximately equal to IAC of the first set.

13. A method for determining a concentration IAC in a volume of a culture medium of a growth-affecting substance affecting a growth of a microbial population deposited on a surface of the culture medium comprising the steps:

depositing the growth-affecting substance at a selected stock concentration SC in a programmed deposition on the surface of the culture medium such that volume of the stock concentration at any deposited location on the surface of the culture medium is determinable;

determining a transformation function TF which accounts for movement of the deposited growth-affecting substance through the culture medium; and calculating IAC at a point of interaction on the culture medium of an interaction of the growth-affecting substance and the microbial population with IAC being a weight per unit volume of the growth-affecting substance at the point of interaction on the culture medium wherein $IAC = SC \times TF$.

14. A method in accordance with claim 13 wherein:
TF comprises a functional relationship of a plurality of quantities with one of the quantities being a function of the programmed deposition DF of the stock concentration.

15. A method in accordance with claim 14 wherein:
the one quantity LDF is a linearization of the programmed deposition function DF.

16. A method in accordance with claim 15 further comprising:
determining a linearized diffused deposition function LDDF from the LDF to account for motion of the growth-affecting substance through the culture medium; and
determining a diffused deposition function DDF from LDDF.

17. A method in accordance with claim 16 wherein:
DDF is a function of at least molecular weight MW of the growth-affecting substance.

18. A method in accordance with claim 17 wherein:
an angle (b) subtended by LDDF and LDF is a function of the molecular weight MW of the growth-affecting substance.

19. A method in accordance with claim 18 wherein:

$$\tan(b) = \frac{kd}{MW}$$

wherein kd is a constant representing diffusion of the growth-affecting substance in a particular set of physical and environmental factors.

20. A method in accordance with claim 17 wherein:
another quantity is at least a function of the height of the culture medium.

21. A method in accordance with claim 13 further comprising:
determining quantitative values of unknown parameters contained in TF.

22. A method in accordance with claim 21 wherein:
the determination of quantitative values of the unknown parameters is obtained from two sets of data with a first set of data being an independent determination of IAC such that concentration of the growth-affecting substance for any data point is not affected by motion of the growth-affecting substance and a second set of data being obtained with the growth-affecting substance deposited in the programmed deposition with differing stock concentrations SC producing an identical IAC so as to alter a location of the point of interaction on the surface of the culture medium.

23. A method in accordance with claim 22 wherein:
the values of some of the unknown parameters are selected such that IAC for the second set of data have a coefficient of variation.

24. A method in accordance with claim 23 wherein:
the value of some of the unknown parameters are selected such that IAC of the second set of data are approximately equal to IAC of the first set.

* * * * *